Figure 1:
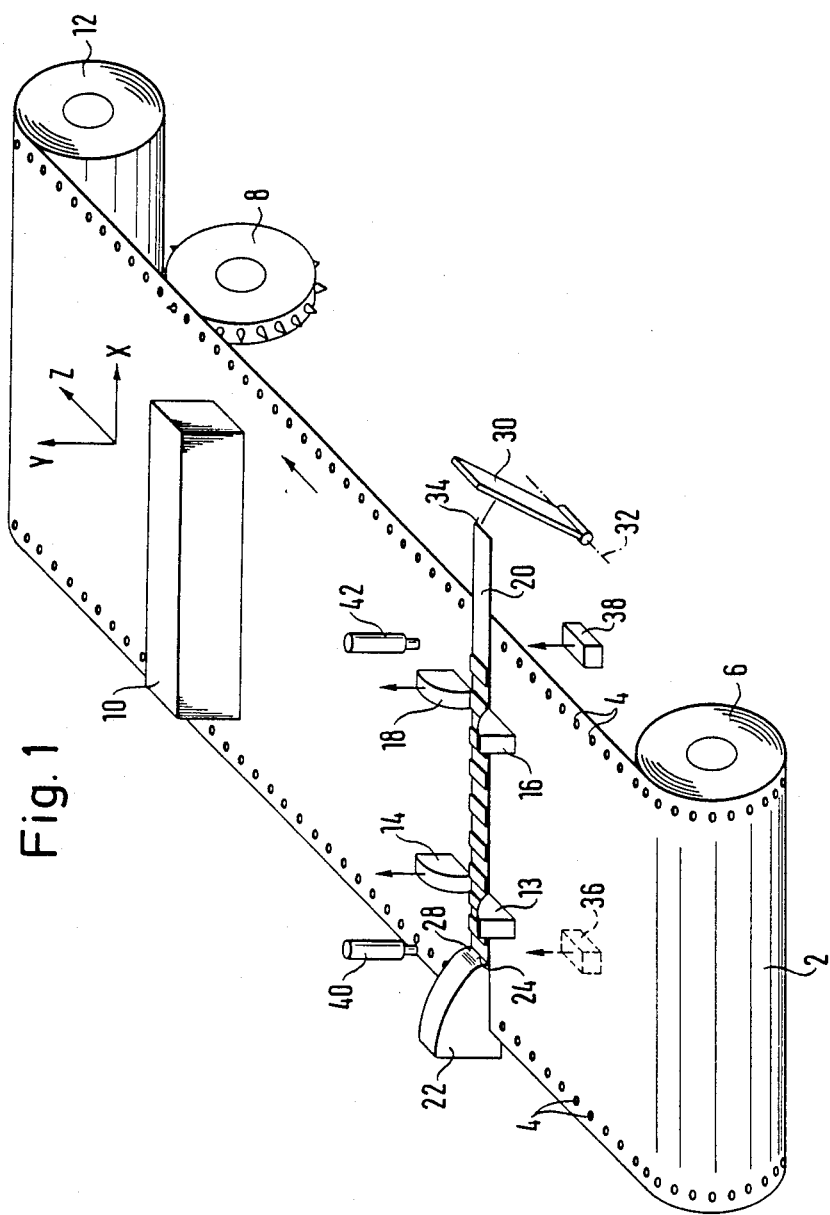

United States Patent [19]

Mann

[11] Patent Number: 4,969,738
[45] Date of Patent: Nov. 13, 1990

[54] CARRIER BAND FOR TEST STRIPS AND DEVICE FOR FIXING TEST STRIPS ON TO A CARRIER BAND

[75] Inventor: Karlheinz Mann, Weilheim, Fed. Rep. of Germany

[73] Assignee: Boehringer Mannheim GmbH, Mannheim-Waldhof, Fed. Rep. of Germany

[21] Appl. No.: 252,818

[22] Filed: Oct. 3, 1988

[30] Foreign Application Priority Data

Oct. 16, 1987 [DE] Fed. Rep. of Germany ....... 3735157

[51] Int. Cl.$^5$ ............................................. G01N 1/28
[52] U.S. Cl. .................................................. 356/244
[58] Field of Search .................... 356/38, 244; 422/66; 436/44

[56] References Cited

U.S. PATENT DOCUMENTS 3,609,045  9/1971  Stein .
3,764,215  10/1973  Wallach .......................... 356/244 X
3,980,437  9/1976  Kishimoto et al. .
4,171,866  10/1979  Tolles .............................. 356/244 X
4,174,178  11/1979  Ouchi et al. ..................... 356/244 X
4,453,406  6/1984  Spitzer ............................. 436/44 X
4,689,202  8/1987  Khoja et al. .

FOREIGN PATENT DOCUMENTS 0054849  5/1985  European Pat. Off. .
2803849  8/1979  Fed. Rep. of Germany .

Primary Examiner—Davis L. Willis
Assistant Examiner—Matthew W. Koren
Attorney, Agent, or Firm—Toren, McGeady & Associates

[57] ABSTRACT

The present invention provides a carrier band which is movable stepwise in its longitudinal direction past an optical measurement device and on its side facing the measurement device carries test strips to be impregnated with a test liquid running transversely to its longitudinal direction, wherein the test strips are fixed on the carrier band at equal distances to one another at least next to the edges of the carrier band. The present invention also provides a device for fixing test strips on to a carrier band.

5 Claims, 2 Drawing Sheets

CARRIER BAND FOR TEST STRIPS AND DEVICE FOR FIXING TEST STRIPS ON TO A CARRIER BAND

The present invention is concerned with a carrier band which is movable stepwise in its longitudinal direction past an optical measurement device and on its side facing the measurement device carries test strips to be impregnated with test liquid running transversely to its longitudinal direction. The present invention is also concerned with a device for fixing test strips to a carrier band.

According to Federal Republic of Germany Patent Specification No. 28 03 849, it is known to introduce the test strips into depressions running parallel to the axis of a roller and, in this state, to move them under a measurement head which is slidably mounted and can thus scan the length of the test strips.

According to U.S. Pat. No. 3,980,437, it is known to place the test strips on a carrier band and to move them by means of the carrier band in their longitudinal direction under a measurement device. An alignment of the test strips thereby does not take place.

As a whole, the known carrier bands with measurement strips and the associated devices for the alignment of the test strips on the carrier band have the following disadvantages:
1. In the case of stepwise movement of the carrier band, the test strips can be caught on any parts of the device which results in faulty measurements.
2. The alignment of the test strips on the carrier band requires a laborious mechanism at the place of measurement.
3. The test strips have a secure alignment to the measurement device only during the measurements, i.e. the test strips must, in each case, be newly aligned when measurements are to take place at several places or other manipulations are necessary on the test strips which require their alignment on the carrier band.
4. The consumption of carrier band material is high since, for the alignment of the test strips on the carrier band, sufficient distances and sufficient step intervals of the carrier band must be present between measurements taking place successively.
5. If an automatic loading of the carrier band with test strips is to take place, then the loading mechanism becomes very complicated.
6. The position of the strips at the point of loading is dependent upon the dexterity of the user.

It is an object of the present invention to provide a carrier band with test strips of the above-described type in which the test strips are previously aligned on the carrier band, i.e. before the measurement, and cannot be changed in their alignment.

Thus, according to the present invention, there is provided a carrier band which is movable stepwise in its longitudinal direction past an optical measurement device and on its side facing the measurement device carries test strips to be impregnated with test liquid running transversely to its longitudinal direction, wherein the test strips are fixed on the carrier band at equal distances to one another at least next to the edges of the carrier band. Since, according to the present invention, the test strips are fixed on the carrier band at equal distances, the following advantages are obtained:

1. Since, due to the fixing, the geometric position of the test strips with respect to the carrier band is maintained, in an apparatus there can be provided at different places devices for dosing test liquid, for heating test fields and for measuring test strips without in each case a new alignment of the test strips on the carrier band being necessary.
2. If necessary, the carrier band can be moved forwards and backwards without any change of the alignment of the test strips on the carrier band.
3. During the stepwise movement of the carrier band, the test strips cannot slip on the carrier band or, since they lie securely flat on the carrier band, do not get caught up on any parts of the device.
4. The consumption of carrier band material is considerably reduced since the distances of the test strips on the carrier band can amount to only a few millimeters. This also permits a reduction of the constructional size of the measurement device or of the possibly provided whole apparatus in the case of correspondingly reduced stepwise speed of the carrier band without the incubation time (i.e. the time between the impregnation of a test strip and the measurement of the impregnated test strip) having to be reduced.
5. The test strips cannot be deformed (bend up or break) on the test band, a tendency which arises especially in the case of impregnated test strips.
6. In the case of fully automatic measurement devices or whole apparatus, the carrier bands can be previously made up with the test strips fixed thereon, especially when the impregnation of the test strips takes place within the apparatus as a whole. The whole apparatus is thereby greatly simplified and is less subject to disturbance in operation.

According to a preferred embodiment of the present invention, the test strips consist, at least on the underside, of a heat-sealable material which is sealed with the carrier band on at least two points lying next to the edges of the carrier band.

According to another preferred embodiment of the present invention, the test strips are fixed to the carrier band by means of staples on at least two points lying next to the edges of the carrier band.

The distance of the test strips from one another on the carrier band can be from 2 to 12 mm.

The present invention also provides an especially simple and operationally reliable device for fixing test strips on to a carrier band comprising a horizontal base over which a carrier band is movable stepwise in its longitudinal direction, positioning pieces arranged above the base for the insertion of the test strips and for the alignment of the test strips in the longitudinal and transverse direction of the carrier band during the stationary periods of the carrier band between its stepwise movement and pressure members arranged above the carrier band and supports arranged below the carrier band for fixing the aligned test strips on the carrier band during the stationary periods of the carrier band between its stepwise movement.

According to a preferred embodiment of the device, a measurement device is provided at a distance of at least one step length of the movement of the carrier band downstream of the pressure members and of the supports.

Figure 2:
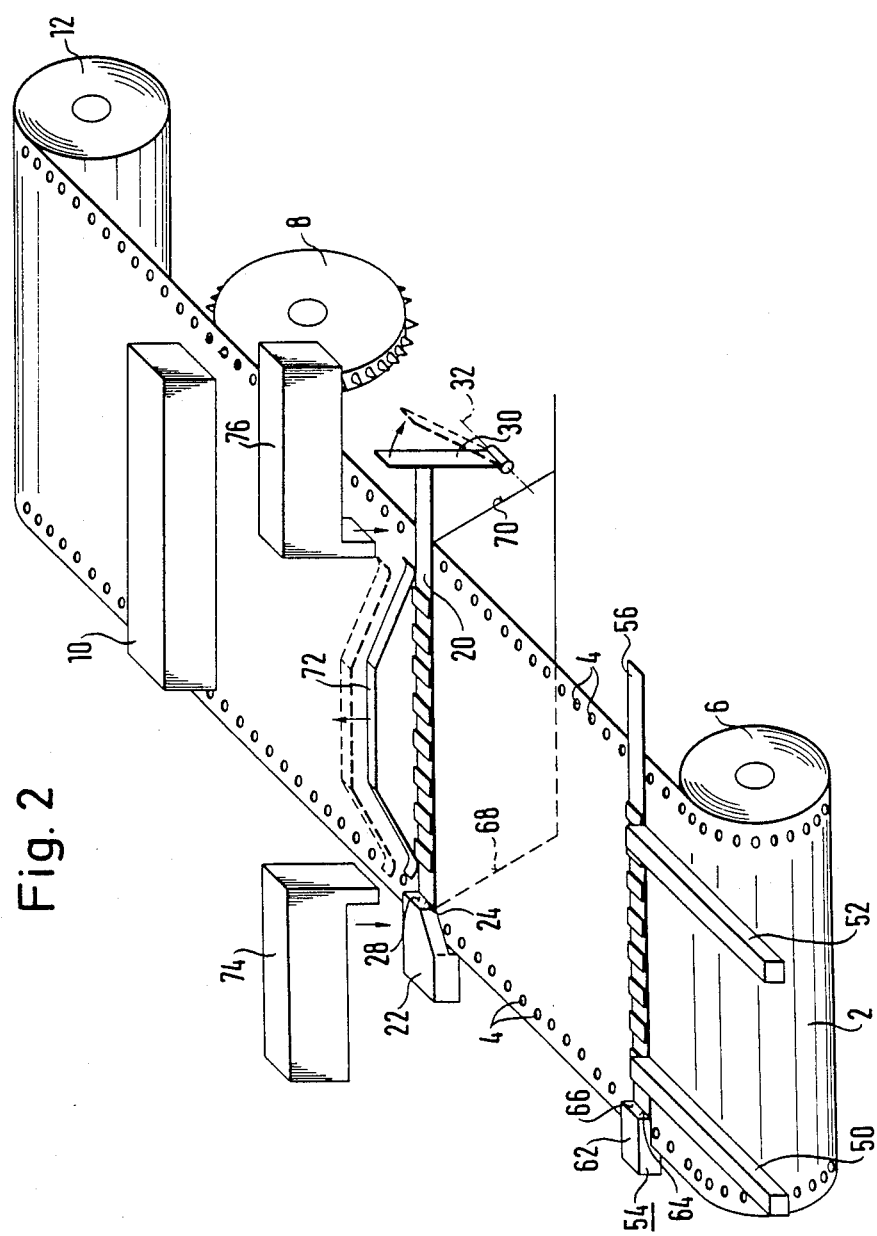

The present invention will now be described in more detail on the basis of two embodiments and with reference to the accompanying drawings, in which FIG. 1 shows the construction of a first device; and FIG. 2 shows the construction of a second device.

The same reference numbers are used for the designation of functionally equivalent elements.

FIGS. 1 and 2 show a carrier band 2 with edge holes 4 which is rolled off from a storage roll 6 and is transported stepwise by means of a toothed roller 8 below an optical measurement device 10 to a winding-up roll 12. The roll of the carrier band 2 with the test strips present thereon which thereby results is waste.

FIG. 1 shows above a horizontal section of the carrier band 2, upstream of the measurement device 10, positioning blocks 13,14,16 and 18 for test strips 20. The lower boundary surfaces of the positioning blocks 13,14,16 and 18 lie, in the illustrated state, close to the carrier band 2. Their upper boundary surfaces are rounded as far as their facing lower edges and form positioning members for the test strips 20. The blocks 13 and 16 are fixed to the device whereas the blocks 14 and 18 are lifted up during the stepwise movement of the carrier band 2 by means which are not illustrated. Next to one edge of the carrier band, there is present a stop block 22, engaging over the carrier band 2, for the end face 24 of the test strip 20 facing it. From the position illustrated in FIG. 1, the test strip 20 is to be pushed up to an edge (in FIG. 1 on the right) of a stop face 28 of the stop block 22. For this purpose, there serves an alignment plate 30 which, in the embodiment according to FIG. 1, is tiltable about an axis 32 fixed to the device and can be tilted to the end face 34 lying opposite the end surface 24 for pushing the test strip 20 up to the stop face 28.

Below the carrier band 2, next to the edges of the carrier band 2, two heat resistances 36 and 38 can be moved up and down simultaneously which cooperate with two press stamps 40 and 42 for sealing the test strip 20 on to the carrier band 2.

As heat resistances 36 and 38, there are used ceramic resistances which are heated to about 150° C. and are guided from below to the carrier band 2 of paper in order to seal test strips of polystyrene on to the carrier band 2. The press stamps 40 and 42 are cold, have a diameter of about 2 mm. and are pressed with a pressure of about 5N against the heat resistances 36 and 38. A pressing on time of 1 to 2 seconds proves to be sufficient even in the case of wet test strips 20.

In the case of the embodiment according to FIG. 2, above the carrier band 2 are provided, at a distance from the measurement device, positioning pieces 50,52 and 54 for the rough alignment of, in each case, one test strip 56 on the carrier band 2. The positioning piece 54 engages with one end 62 over the carrier band 2 and has a stop face 66 for the end face 64 of the test strip 56.

At a distance of a whole number of step lengths of the carrier band 2 there is present a flexible grate 72, which can be moved up and down, for the test strip 20 which is lowered before the conclusion of the carrier band forward movement and aligns the test strip at rightangles to the direction of the carrier band and a further stop piece 22 which, corresponding to FIG. 1, stands opposite to a stop plate 30 on the other edge of the carrier band 2. At this place, there takes place a fine alignment of the test strip 20 by impingement on the stop surface 28 of the stop piece 22 and impingement on the grate 72.

Below the carrier band 2 are provided, in a nonillustrated base, troughs 68 and 70 for the shaping of staples. Above the troughs 68 and 70 are provided staple suppliers 74 and 76 which can be moved up and down.

I claim:

1. A carrier band (2) which is movable stepwise in its longitudinal direction past an optical measurement device (10) and on its side facing the measurement device (10) carries test strips (20) to be impregnated with a test liquid running transversely to its longitudinal direction, wherein the test strips (20) are fixed on the carrier band (2) at equal distances to one another at least next to the edges of the carrier band (2), the test strips (20) having, at least on the underside, a heat-sealable material which is sealed with the carrier band (2) on at least two points lying next to the edges of the carrier band (2).

2. A carrier band (2) which is movable stepwise in its longitudinal direction past an optical measurement device (10) and on its side facing the measurement device (10) carries test strips (20) to be impregnated with a test liquid running transversely to its longitudinal direction, wherein the test strips (20) are fixed on the carrier band (2) at equal distances to one another at least next to the edges of the carrier band (2), the test strips (20) being fixed to the carrier band (2) by means of staples on at least two points lying next the edges of the carrier (2).

3. A carrier band according to claim 1 or 2, wherein the distance of the test strips (20) from one another is from 2 to 12 mm.

4. A device for fixing test strips (20) on to a carrier band (2), comprising a horizontal base over which a carrier band (2) is movable stepwise in its longitudinal direction, positioning pieces (13, 14, 16, 18, 22; 50, 52, 54, 22) arranged above the base for the insertion of test strips (20) and for alignment of the test strips (20) in logitudinal and transverse directions of the carrier band (2) during stationary periods of the carrier band (2) between its stepwise movement and pressure members (40, 42; 74, 76) arranged above the carrier band (2) and supports (36, 38; 68, 70) arranged below the carrier band (2) for fixing the aligned test strips (2) on the carrier band (2) during the stationary periods of the carrier band (2) between its stepwise movement.

5. A device according to claim 4, wherein a measurement device (10) is provided at a distance of at least one step length of the movement of the carrier band (2) downstream of the pressure members (40,42; 74,76) and of the supports (36,38; 68,70).

* * * * *